(12) United States Patent
McDevitt et al.

(10) Patent No.: US 7,846,913 B2
(45) Date of Patent: Dec. 7, 2010

(54) COMPOSITIONS AND METHODS TO TREAT RECURRENT MEDICAL CONDITIONS

(76) Inventors: Jason Patrick McDevitt, 124 Country Club Dr., Williamsburg, VA (US) 23188; Michael Davis, 5570 Oakwood Dr., Stone Mountain, GA (US) 30087

( * ) Notice: Subject to any disclaimer, the term of this patent is extended or adjusted under 35 U.S.C. 154(b) by 1654 days.

(21) Appl. No.: 11/024,921

(22) Filed: Dec. 29, 2004

(65) Prior Publication Data
US 2005/0143314 A1 Jun. 30, 2005

Related U.S. Application Data

(60) Provisional application No. 60/533,003, filed on Dec. 29, 2003, provisional application No. 60/625,253, filed on Nov. 5, 2004.

(51) Int. Cl.
*A01N 43/04* (2006.01)
*A61K 31/70* (2006.01)

(52) U.S. Cl. ..................................... 514/52
(58) Field of Classification Search ............ 514/52
See application file for complete search history.

(56) References Cited

U.S. PATENT DOCUMENTS

| | | | |
|---|---|---|---|
| 5,061,721 A | 10/1991 | Cordi | |
| 5,086,072 A | 2/1992 | Trullas | |
| 5,260,324 A | 11/1993 | Cordi | |
| 5,428,069 A | 6/1995 | Skolnick | |
| 5,523,323 A | 6/1996 | MacCecchini | |
| 6,133,281 A * | 10/2000 | Gonzalez-Cadavid et al. | 514/289 |
| 6,228,875 B1 | 5/2001 | Tsai | |
| 6,333,357 B1 | 12/2001 | Elg | |
| 6,355,681 B2 | 3/2002 | Javitt | |
| 6,420,351 B1 | 7/2002 | Tsai | |
| 6,667,297 B2 | 12/2003 | Tsai | |
| 2001/0053780 A1* | 12/2001 | Whitaker et al. | 514/250 |
| 2002/0146471 A1* | 10/2002 | Wuh et al. | 424/728 |
| 2004/0208923 A1* | 10/2004 | Davis et al. | 424/464 |
| 2005/0096396 A1 | 5/2005 | Davis | |

FOREIGN PATENT DOCUMENTS

WO   WO-02078629 A2   10/2002

OTHER PUBLICATIONS

Nurnberg (Depression, Antidepressant therapies, and Erectile Dysfunction: Clinical Trial of Sildenafil Citrate (Viagra®) in Treated and Untreated Patients with Depression, Urology 60 (Suppl 2B); pp. 58-66, 2002).*
Papp (Antidepressant-like effects of 1-aminocyclopropanecarboxylic acid and D-cycloserine in an animal model of depression, European Journal of Pharmacology 316 (1996) pp. 145-151).*
Birk, "Pharmacotherapy for Performance Anxiety Disorders . . . ", Journal of Clinical Psychology, (2004), vol. 60(8), p. 867-879.
Ressler, "Cognitive Enhancers as Adjuncts to Psychotherapy", Archives of General Psychiatry, (2004); vol. 61, p. 1136-1144.
Mothet, "D-Serine is an endogenous ligand for the glycine site . . . ", Proc. Natl. Acad. Sci. USA., (2000), vol. 97(9), p. 4926-4931.
Van Berckel, "Behavioral and Neuroendocrine Effects of the Partial NMDA . . . ", Neuropsychopharmacology, (1997), vol. 16(5), p. 317-324.
Wager, "Placebo-Induced Changes in fMRI in the Anticipation and Experience of Pain", Science, (2004), vol. 303, p. 1162-1167.
Yamakura, "Subunit- and Site-Specific Pharmacology of the NMDA Receptor Channel", Progess in Neurobiology, (1999), vol. 59, p. 279-298.
Boje, "Desensitization of the NMDA Receptor Complex by Glycinergic Ligands . . . ", Brain Research, (1993), vol. 603(2), p. 207-214.
Walker, "Facilitation of Conditioned Fear Extinction by Systemic Administration . . . ", The Journal of Neuroscience, (2002), vol. 22, p. 2343-2351.
Heresco-Levy, "Placebo-Controlled Trial of D-Cycloserine Added to Conventional Neuroleptics . . . ", Am. J. Psychiatry, (2002), vol. 159(3), p. 480-482.

* cited by examiner

*Primary Examiner*—San-ming Hui
*Assistant Examiner*—Kathrien Cruz
(74) *Attorney, Agent, or Firm*—Jason P. McDevitt

(57) ABSTRACT

The invention describes methods and compositions for alleviating recurrent medical afflictions for which anxiety may cause or exacerbate the affliction. A subject suffering from the affliction is treated with a combination of a pharmaceutical that enhances learning, and a second pharmaceutical recognized to be useful for treatment of the affliction. Representative afflictions include insomnia, erectile dysfunction, female sexual dysfunction, neuropathic pain, attention deficit disorder, and depression.

3 Claims, No Drawings

COMPOSITIONS AND METHODS TO TREAT RECURRENT MEDICAL CONDITIONS

CROSS-REFERENCE TO RELATED APPLICATIONS

This application is based upon and claims priority to the following United States provisional patent applications: U.S. Provisional Application No. 60/533,003, filed Dec. 29, 2003; and U.S. Provisional Application No. 60/625,253, filed Nov. 5, 2004.

STATEMENT REGARDING FEDERALLY SPONSORED RESEARCH OR DEVELOPMENT

Not Applicable

BACKGROUND OF THE INVENTION

Widely prescribed pharmaceuticals for health disorders such as insomnia and erectile dysfunction target only the biochemical physiology of the affliction, ignoring the psychological component. This is a wasted opportunity, since as a byproduct of successful physiological outcomes, drugs for disorders such as insomnia and erectile dysfunction can provide afflicted individuals with temporary relief of anxiety associated with the condition. However, this psychological "fix" is only temporary, and existing pharmaceutical therapies neglect the opportunity to capture or consolidate the favorable psychological response. Instead, an afflicted individual's anxiety regarding the disorder can return, often provoking or exacerbating a relapse of the disorder.

Classical fear conditioning occurs when an affectively neutral stimulus is paired with a noxious aversive stimulus (unconditioned stimulus [US]) such as footshock. Afterward, the previously neutral stimulus (i.e., now the conditioned stimulus [CS]) is able to elicit a variety of autonomic, hormonal, and skeletal responses that accompany the conscious experience of fear in humans and which are used to operationally define fear in laboratory animals. The fear-eliciting properties of the CS can be extinguished by repeatedly presenting the CS in the absence of the US. It is generally believed that extinction does not reflect unlearning of the original association but involves instead the formation of new associations that compete with the previously conditioned response.

Recent results in the field of cognitive neuroscience have demonstrated that a drug that enhances learning can consolidate a favorable psychological response to a stimulus (WO 02/078629, incorporated herein by reference in its entirety). This result has been very important in the treatment of phobic disorders, as a recent clinical study has shown that subjects undergoing cognitive behavioral therapy require substantially fewer sessions to reach clinical cure (e.g., 75% fewer) if they are administered a drug that enhances learning in conjunction with their therapy sessions (Davis, *Arch Gen Psychiatry*. 2004; 61: 1136-1144). A suitable drug for enhancing learning is D-cycloserine ("DCS"). DCS is an FDA-approved, off-patent, second-line treatment for tuberculosis (trade name Seromycin®, hereafter "DCS", sold by Eli Lilly), with a side effect of enhanced learning, although chronic administration tends to limit or even reverse this effect. Other cognitive enhancers, in particular other glycine partial NMDA receptor agonists, are also believed to be effective.

Accordingly, the prior art describes treatments for phobic disorders comprising behavioral cognitive therapy in conjunction with acute administration of pharmaceuticals that enhance learning.

The prior art also describes chronic administration of NMDA agonists to treat Alzheimer's Disease and neuropsychiatric disorders. U.S. Pat. No. 6,228,875 describes administering 105-500 mg doses of DCS (or other NMDA receptor agonists) on a chronic basis to treat schizophrenia, attention deficit disorder, and other neuropsychiatric disorders. It does not teach the advantages of administering acute doses of DCS in conjunction with other drugs.

The prior art does not describe treatments of other disorders such as depression, insomnia, erectile dysfunction, and chronic pain by combining pharmaceutical treatments for those conditions with acute administration of pharmaceuticals that enhance learning.

There is a long-felt need in the art for compositions and methods for enhancing the treatment of diseases and disorders which have anxiety components. The present invention satisfies those needs.

BRIEF SUMMARY OF THE INVENTION

The invention describes methods and compositions for alleviating recurrent medical afflictions for which anxiety may cause or exacerbate the affliction. A subject suffering from the affliction is treated with a combination of:

(1) a pharmaceutical compound that enhances learning (the secondary drug), and (2) a second pharmaceutical compound (the primary drug) that is recognized as effective for alleviating the specific affliction.

Our technology utilizes one or more partial NMDA receptor agonists as a learning-enhancing secondary drug that improves the efficacy of a primary drug by locking in the psychological benefits derived from treatment with the primary drug. Relative to subjects treated with only the second pharmaceutical compound, i.e., only the primary drug, the affliction is, on average, alleviated to a greater extent in subjects treated with the pharmaceutical combination that includes the compound that enhances learning. The beneficial effects of the methods and compositions of the present invention are frequently not observed in traditional biochemical assays, since these benefits are focused on the whole mind/body response of the subject rather than on a simple biochemical target at the molecular or cellular level.

Representative disorders that can be treated according to the methods and compositions of the invention include insomnia, erectile dysfunction, female sexual dysfunction, neuropathic pain, attention deficit-hyperactivity disorder, depression, and anxiety disorders. For some recurrent medical afflictions, the afflictions are transient, and can be treated by acute administration of a pharmaceutical. Notable examples are erectile dysfunction and female sexual dysfunction. Several other afflictions for which there may be an associated, underlying psychological component are customarily treated via repeated daily administration of pharmaceuticals. Representative afflictions include insomnia (also treated sometimes on an acute basis), chronic pain, neuropathic pain, anxiety, depression, and attention deficit-hyperactivity disorder, among others. The invention described herein contemplates methods and compositions for alleviating these recurrent medical afflictions comprising administering to the subject:

(1) a compound that alleviates the specific condition, and (2) a compound that enhances learning, wherein the compound that treats the specific condition is dosed on average at least once every 24 hours, and wherein the compound that enhances learning, preferably an NMDA partial receptor agonist, is administered to the subject with reduced frequency, not to exceed two times per week.

In embodiments wherein DCS is used the compound that enhances learning, then if DCS is dosed on a more frequent basis, i.e., daily, or three or more times a week, then it will not have a significant positive effect as a learning enhancer, and may have a negative effect.

DETAILED DESCRIPTION OF THE INVENTION

As used herein, each of the following terms has the meaning associated with it as described below.

The articles "a" and "an" are used herein to refer to one or to more than one (i.e. to at least one) of the grammatical object of the article. By way of example, "an element" means one element or more than one element.

As used herein, "plurality" means at least two.

As used herein, "FDA" means the United States Food and Drug Administration.

Any ranges cited herein are inclusive, e.g., "between about 50 mg and 100 mg" includes compositions of 50 mg and 100 mg.

As used herein, "acute" administration of a therapeutic means a single exposure within an extended time period of the subject to the therapeutically effective amount of the pharmacologic agent that enhances learning or conditioning. In conjunction with this definition of "acute", an extended time period is defined as four days or longer, e.g., once-weekly administration of DCS constitutes acute administration. Administering a dose of DCS to a subject, followed by a second dose 24 hours later, does not constitute acute dosing. Administering a single dose of DCS, wherein the dose is formulated to have both immediate release and delayed release characteristics, constitutes acute dosing provided that the peak blood level of DCS in the subject is achieved within 12 hours of the time the dose is administered.

A "disease" is a state of health of an animal (mammal) wherein the animal cannot maintain homeostasis, and wherein if the disease is not ameliorated, then the animal's health continues to deteriorate. In contrast, a "disorder" in an animal is a state of health in which the animal is able to reasonably maintain homeostasis, but in which the animal's state of health is less favorable than it would be in the absence of the disorder. Left untreated, a disorder does not necessarily cause a further decrease in the animal's state of health.

As used herein, "a recurrent medical affliction" refers to a recurring or chronic disorder in a human that can be caused or exacerbated, at least in some individuals, by anxiety or stress about the disorder. For the purposes of this definition, "anxiety" or "stress" is a state of concern, or worry, or apprehension, or psychological discomfort, about the disorder. Anxiety or stress may be acknowledged by a subject, or may be present without the subject's awareness. Anxiety about the disorder is not required in every subject in order for the disorder to be defined as a recurrent medical affliction; on the contrary, a disorder fits the definition if some subjects are anxious or stressful about the disorder some of the time. For purposes of the present invention, an individual said to have a recurrent medical affliction will have one or more disorders that can be treated with the methods of the invention. Thus an individual may have a single disorder, or may have a constellation of disorders that can be treated by the methods described herein. The recurrent medical afflictions contemplated in the present invention include, but are not limited to, erectile dysfunction, female sexual dysfunction, chronic pain, neuropathic pain, insomnia, attention deficit-hyperactivity disorder, addiction, fatigue, anxiety disorders, depression, migraine headaches, and eating disorders.

As used herein, a subject is "treated", or subjected to "treatment", when an earnest attempt is made to alleviate a medical disorder or disease. For example, a subject can be treated for a disorder by being administered a pharmacologic agent that is intended to alleviate the disorder, irrespective of whether the treatment actually was successful in alleviating the disorder.

As used herein, a disease or disorder or recurrent medical affliction is "alleviated" if the severity of a symptom of the disease or disorder or recurrent medical affliction, the frequency with which such a symptom is experienced by a subject, or both, are reduced.

A "subject" of diagnosis or treatment is a human.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, a "B-complex vitamin" is one or more vitamins selected from the group comprising thiamine (B1), riboflavin (B2), niacin (B3), pyridoxine (B6), folic acid (B9), cyanocobalamin (B 12), pantothenic acid and biotin.

It will be appreciated that when using a combination method of the present invention, both the compound that enhances learning and the primary drug compound generally known to be useful for alleviating the recurrent medical affliction will be administered to a subject within a reasonable period of time (e.g., within 12 hours, preferably within four hours). The compounds may be in the same pharmaceutically acceptable carrier and therefore administered simultaneously. They may be in separate pharmaceutical carriers such as conventional oral dosage forms that are taken simultaneously. The term combination, as used above, also refers to the case where the compounds are provided in separate dosage forms and are administered sequentially, provided they are administered within a period of twelve hours, preferably within four hours.

As used herein, the term "depression" includes depressive disorders, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias, seasonal affective disorder, or bipolar disorders or manic depression, for example, bipolar I disorder, bipolar II disorder and cyclothymic disorder.

As used herein, the term "neuropathic pain" means pain that originates from a damaged or malfunctioning nerve or nervous system. "Chronic pain" means pain that has lasted for more than three months, generally resulting in significant psychological and emotional affects and limiting a person's ability to fully function.

As used herein, "insomnia" is defined as the inability to fall asleep or to stay asleep for a sufficient amount of time during regular sleeping hours. It includes acute insomnia, which occurs in either a transient or short term form, and chronic insomnia. It also includes initial insomnia, defined as difficulty in falling asleep; middle insomnia, defined as awakening in the middle of the night followed by eventually falling back to sleep, but with difficulty; and terminal insomnia, defined as awakening before one's usual waking time and being unable to return to sleep.

As used herein, "attention deficit-hyperactivity disorder", sometimes referred to as attention deficit disorder, is defined as a disorder in individuals characterized by serious and persistent difficulties relating to inattentiveness, distractability, impulsivity, and hyperactivity.

As used herein, "erectile dysfunction" is impotence resulting from a man's inability to obtain or maintain an erection of his penis.

As used herein, "female sexual dysfunction" is characterized by an unwanted lack of desire, arousal, or orgasm. The American Psychological Association (APA) classifies female sexual problems as mental disorders: loss of sexual desire or arousal, discomfort during intercourse, diminished blood flow to the vagina, trauma-related aversion to sex, and the inability to achieve orgasm.

As used herein, a compound that "enhances learning", or is a "cognitive enhancer", is any pharmacologic agent that is recognized by the skilled artisan as being a pharmacologic agent that can improve cognitive function when used in accordance with the methods of the invention. For example, one class of such pharmacologic agents are those compounds that increase the level of acetylcholine in the brain, including, for example, compounds that block the breakdown of acetylcholine. Examples of such compounds include, but are not limited to, donepezil, E2020 and tacrine, which inhibit cholinesterase activity. Another class of compounds that enhance learning are pharmacologic agents that enhance N-methyl-D-aspartate (NMDA) receptor activation or transmission (cation flow) in the brain. Particularly useful are pharmacologic agents that enhance N-methyl-D-aspartate (NMDA) receptor activation or transmission (cation flow) in the brain without causing significant neurotoxicity. Such enhanced NMDA receptor transmission can be measured by a variety of methods known to the skilled artisan. For example, Luteinizing Hormone (LH) secretion is used as a measure of NMDA receptor activation (see van Berckel et al. (1997) *Neuropsychopharm.* 16(5): 317-324). Other methods include electrophysiological and chemical methods (see Mothet et al. (2000) *Proc. Natl. Acad. Sci. USA* 97(9): 4926-4931). Neurotoxicity can be measured by, for example, the cultured cerebellar granule neuron system described in Boje et al. (1993) *Brain Res.* 603(2): 207-214.

As used herein, the term "NMDA receptor" or "NMDA channel" refers to the glutamate receptor channel NMDA subtype (Yamakura and Shimoji (1999) *Prog. Neurobiol.* 59(3): 279-298). The term "agonist" encompasses any compound that increases the flow of cations through an ionotrophic receptor such as the NMDA receptor, i.e., a channel opener, and which has not been observed to decrease the flow of cations through the same receptor. "Antagonist" includes any compound that reduces the flow of cations through an ionotropic receptor such as the NMDA receptor, i.e., a channel closer, and which has not been observed to increase the flow of cations through the same receptor. The term "partial agonist" refers to a compound that regulates an allosteric site on an ionotropic receptor, such as the NMDA receptor, to increase or decrease the flux of cations through the ligand-gated channel depending on the presence or absence of the principal site ligand, that is, in the presence or absence of a known endogenous ligand binding to a site on the receptor. In the absence of the principal site ligand, a partial agonist increases the flow of cations through the ligand-gated channel, but at a lower flux than achieved by the principal site ligand. A partial agonist partially opens the receptor channel. In the presence of the principal site ligand, a partial agonist decreases the flow of cations through the ligand-gated channel below the flux normally achieved by the principal site ligand. As used herein, "NMDA receptor agonist," "NMDA receptor antagonist," and "NMDA receptor partial agonist," may be alternately referred to as "NMDA agonist," "NMDA antagonist," and "NMDA partial antagonist," respectively. Also, "NMDA receptor partial agonist" is intended to be interchangeable with "partial NMDA receptor agonist." The present invention contemplates a variety of molecules acting as such partial NMDA receptor agonists. Examples of such pharmacologic agents include, but are not limited to, compounds that act at the glycine modulatory site of the NMDA receptor, including DCS, D-serine, and 1-aminocyclopropane-carboxylic acid (ACPC) (see U.S. Pat. Nos. 5,086,072 and 5,428,069, herein incorporated by reference). NMDA receptor partial agonists are compounds that can enhance learning, and are particularly useful when used in accordance with the methods and compositions of the present invention.

DCS has been FDA-approved for approximately 20 years for the treatment of tuberculosis. It has been tested as a cognitive enhancer in several clinical trials over the last decade. For tuberculosis, DCS is generally dosed at 500-1000 mg/day divided twice daily (PDR 1997) with chronic treatment. At a dose of 500 mg/day, blood levels of 25-30 mg/ml are generally maintained. The peak blood levels occur within 3-8 hours after dosing, and it is primarily renally excreted with a half-life of 10 hours. Infrequent side effects in subjects on chronic dosing schedules (who were generally chronically ill with tuberculosis) include drowsiness, headache, confusion, tremor, vertigo, and memory difficulties, paresthesias, and seizure. Side effects correlate well with dosage amount.

In the United States, DCS is approved as a pharmaceutical for treatment of tuberculosis in dosages of 250 mg (Seromycin®, available from Eli Lilly). The relatively high concentration of active ingredient is necessary to provide sufficient bactericidal activity. However, the cognitive enhancing effects of DCS can be obtained at a much lower dose. Accordingly, the methods and compositions of the present invention preferably comprise administration of DCS to subjects in concentrations ranging from about 25 mg to about 100 mg, thereby avoiding or reducing some of the side effects associated with DCS, and also providing a sub-antimicrobial dose of the medication.

DCS has also been reported to reduce the levels of certain important chemicals in the blood of subjects, including calcium, folic acid, magnesium, vitamin K, vitamin B6, and vitamin B12. Co-administration of DCS with supplements of any of these ingredients is contemplated by the methods and compositions of this invention. In particular, supplementation of DCS with vitamin B6, vitamin B12, or combinations thereof is contemplated. In one embodiment, a tablet containing 50 mg DCS also contains 50 mg pyridoxine. In other embodiments of the invention, pyridoxine is supplemented at levels up to ten times the dosage of DCS.

While DCS is the preferred compound useful in the methods and compositions of the invention for enhancing learning, other learning enhancers are also contemplated. In particular, other NMDA partial receptor agonists are contemplated. DCS analogs and prodrugs are also contemplated by the methods and compositions of the invention, as are pharmaceutically acceptable salts of DCS, including organic acid salts formed with acids which form a physiological acceptable anion, for example, tosylate, methanesulfonate, acetate, citrate, malonate, tartarate, succinate, benzoate, ascorbate, α-ketoglutarate, and α-glycerophosphate, as well as suitable acid addition salts of inorganic acids including hydrochloride, sulfate, nitrate, bicarbonate, and carbonate salts.

Any pharmacologic agent that is recognized by the skilled artisan as being a pharmacologic agent that is useful for alleviating a recurrent medical condition can be used as the primary drug in accordance with the methods and compositions of the invention.

Erectile Dysfunction

Any pharmacologic agent that is useful for alleviating erectile dysfunction can be used in the methods and compositions of the invention. Erectile dysfunction is the inability to obtain and maintain a penile erection sufficient for satisfactory intercourse or other sexual expression. A number of factors can place an individual at risk for this disorder, for example, trauma, pelvic surgery, hypercholesterolemia, ischemic heart disease, peripheral vascular disease, chronic renal failure, diabetes, or the use of medicaments such as antihypertensive medication or digoxin, or illicit drugs, cigarettes or alcohol. Methods for the treatment of erectile dysfunction include the use of vacuum devices and penile implants, as well as the administration of medicaments such as yohimbine, papaverine and apomorphine, as well as treatment with phosphodiesterase-5 (PDE-5) inhibitors such as vardenafil, tadalafil, and sildenafil. PDE-5 inhibitors enhance a man's ability to obtain and maintain erections. There are other drugs in clinical trials for treatment of erectile dysfunction that target other physiological pathways. For example, PT-141, from Palatin Technologies, targets the central nervous system. Endothelin antagonists are another class of compounds proposed for treatment of erectile dysfunction. The pharmacological treatments for erectile dysfunction are normally quite effective, but they do not cure the affliction or reverse the underlying problems; rather, they only have an acute, temporary benefit. Pharmaceutical compositions comprising a combination of DCS and one or more erectile dysfunction pharmaceutical agents are likely to provide many subjects with significant benefits relative to pharmaceutical compositions comprising the erectile dysfunction pharmaceutical agent but lacking DCS.

There are many causes of erectile dysfunction, and the etiology is strictly psychogenic (i.e., all in the mind) in only about 10-20% of cases. That having been said, performance anxiety complicates many cases for which the primary cause is physiological. Sildenafil has been used successfully to treat subjects whose etiology was believed to be purely psychogenic. For example, Birk (Birk, (2004) Journal of Clinical Psychology, Vol 60(8), 867-879) describes a subject with paralytic sexual performance anxiety, completely unresponsive to purely behavioral interventions. The subject responded to pharmaceutical treatment with sildenafil, and developed an increasing confidence in his predictable sexual functioning. Treatment with sildenafil provided a psychological endpoint very similar to that achieved with successful psychotherapy.

A combination of DCS and sildenafil will facilitate a subject's consolidation of a confident response to a sexual situation, thereby reducing the time necessary to replace the previous negative response to the stimulus with a more positive response. In other words, a reduced number of successful pharmacological interventions are required to reach the same desired psychological end point, which is elimination of deleterious performance anxiety. After several treatments with a combination of effective doses of DCS and sildenafil, a man's performance anxiety can be reduced or eliminated, ideally replaced by a feeling of confidence that actually contributes to improved performance. Since fewer pharmaceutical interventions would be required to eliminate the deleterious performance anxiety, there is less chance that one would go awry (which would damage the newly learned psychological response).

In a clinical trial involving subjects having specific phobias, subjects provided with DCS in conjunction with psychotherapy required an average of only two sessions to reach a clinical cure, while subjects treated with psychotherapy alone required an average of eight sessions (Davis, Arch Gen Psychiatry. 2004; 61: 1136-1144). We have not yet conducted a human clinical study to determine the analogous numbers for sexual performance anxiety.

A compound that is useful for treatment of erectile dysfunction, particularly a PDE-5 inhibitor selected from the group consisting of sildenafil, vardenafil, and tadalafil, normally provides a physiological performance boost sufficient to overcome the deleterious performance anxiety in subjects, thereby producing a successful sexual outcome. When administered in conjunction with the compound that is useful for treatment of erectile dysfunction, a compound that enhances learning consolidates the positive psychological benefits attributable to the successful pharmacotherapy.

In one embodiment, after a course of treatment ranging from one to ten pharmaceutical interventions using a combination of DCS and an appropriate PDE-5 inhibitor, deleterious performance anxiety in a subject with erectile dysfunction should be substantially eliminated. Therefore and thereafter, the physiological boost required for successful sexual performance is reduced. For erectile dysfunction subjects for whom the etiology is primarily psychogenic, this removal of deleterious performance anxiety may be sufficient to cure the subject, eliminating the need for future pharmaceutical intervention. For erectile dysfunction subjects with significant physiological impediments to achieving or maintaining erections, pharmaceutical therapy may still be required; however, the success rate of that pharmaceutical therapy will be higher, as the physiological boost provided by the drug will no longer have to overcome the additional impediment of negative performance anxiety. In other words, even if it does not provide a cure, the combination of DCS and one or more PDE-5 inhibitors can improve the efficacy of ongoing treatments by eliminating the negative influence of performance anxiety. Accordingly, the methods and compositions of the invention are useful for the treatment of most erectile dysfunction subjects, not limited to those subjects for whom the affliction is primarily psychogenic.

In one embodiment, the invention contemplates pharmaceutical compositions of DCS (between 10 mg and 500 mg, preferably between about 25 mg and 250 mg) and sildenafil, sildenafil citrate, or other pharmaceutically appropriate salts of sildenafil (between 10 mg and 200 mg, preferably 25 mg, 50 mg, or 100 mg). In another embodiment, the invention contemplates pharmaceutical compositions comprising DCS (between 10 mg and 500 mg, preferably between about 25 mg and 250 mg) and tadalafil, or any pharmaceutically appropriate salt thereof (between 2.5 mg and 50 mg, preferably 5 mg, 10 mg, or 20 mg). In another embodiment, the invention contemplates pharmaceutical compositions comprising DCS (between 10 mg and 500 mg, preferably between about 25 mg and 250 mg) and vardenafil, vardenafil hydrochloride, or other pharmaceutically appropriate salts of vardenafil (between 2.5 mg and 50 mg, preferably 5 mg, 10 mg, or 20 mg). In other embodiments, the invention also contemplates pharmaceutical compositions comprising combinations of DCS and a second compound selected from the group consisting of yohimbine, PT-141, papaverine, and apomorphine.

Representative methods of the invention include administration of drug combinations such as those described above to subjects suffering from erectile dysfunction. In other methods of the invention, subjects are administered two separate pharmaceutical entities, one of which is a drug useful for treatment of erectile dysfunction, and the second of which is a learning enhancer. In preferred embodiments of that method, the drug useful for treatment of erectile dysfunction is a PDE-5 inhibitor, and the learning enhancer is an NMDA partial receptor agonist. In one embodiment thereof, the NMDA partial receptor agonist is DCS, or a pharmaceutically acceptable salt thereof.

In many embodiments, DCS and a PDE-5 inhibitor will be co-administered. In other embodiments, DCS can be administered within twelve hours prior or subsequent to administration of the PDE-5 inhibitor. Since DCS acts to consolidate learning after a learning event, it is conceivable to administer DCS after a successful treatment with a PDE-5 inhibitor.

Female Sexual Dysfunction

Many pharmacologic agents that have been approved or suggested for treatment of male erectile dysfunction have also been suggested or attempted as treatments for female sexual dysfunction. For example, the following agents have been tested, on either an acute or chronic basis, for treatment of female sexual dysfunction: alprostadil, phentolamine, estradiol, flibanserin, apomorphine, bupropion, testosterone, sildenafil, PT-141, vardenafil, yohimbine, tadalafil, and combinations thereof. These agents are sometimes administered orally, and in other cases are administered as creams, inhalation sprays, or transdermally. The invention contemplates methods and compositions for alleviating female sexual dysfunction comprising administering to a female subject a combination of (i) one or more of the above-listed drugs, and (ii) a compound that enhances learning, preferably DCS.

In general, it is believed that psychological issues contribute to a greater extent in female sexual dysfunction than in male erectile dysfunction. The methods and compositions of the present invention are useful when DCS is combined with a pharmacologic agent wherein the primary mode of action of the pharmacologic agent is concentrated on the central nervous system rather than vascular blood flow. Examples of such pharmacologic agents include apomorphine, bupropion, and PT-141.

In many embodiments of the invention, DCS and a primary drug useful for treating female sexual dysfunction will be co-administered on an acute basis prior to an expected romantic situation. In one such embodiment, a pharmaceutical composition useful for the alleviating female sexual dysfunction comprises DCS (between 10 mg and 500 mg, preferably between about 25 mg and 250 mg) and sildenafil, sildenafil citrate, or other pharmaceutically appropriate salts of sildenafil (between 5 mg and 200 mg, preferably between 10 mg and 100 mg). In another embodiment, a pharmaceutical composition useful for alleviating female sexual dysfunction comprises DCS (between 10 mg and 500 mg, preferably between about 25 mg and 250 mg) and tadalafil, or any pharmaceutically appropriate salt thereof (between 1 mg and 50 mg, preferably between 2 mg and 20 mg). In another embodiment, a pharmaceutical composition useful for alleviating female sexual dysfunction comprises DCS (between 10 mg and 500 mg, preferably between about 25 mg and 250 mg g) and vardenafil, vardenafil hydrochloride, or other pharmaceutically appropriate salts of vardenafil (between 1 mg and 50 mg, preferably between 2 mg and 20 mg). In another embodiment, a pharmaceutical composition useful for alleviating female sexual dysfunction comprises DCS (between 10 mg and 500 mg, preferably between about 25 mg and 250 mg) and PT-141, or a pharmaceutically acceptable salt thereof (between 2 mg and 20 mg). In another embodiment, a pharmaceutical composition useful for alleviating female sexual dysfunction comprises DCS (between 10 mg and 500 mg, preferably between about 25 mg and 250 mg) and apomorphine hydrochloride (between about 2 mg and 25 mg). In another embodiment, a pharmaceutical composition useful for alleviating female sexual dysfunction comprises DCS (between 10 mg and 500 mg, preferably between about 25 mg and 250 mg) and bupropion (between about 30 mg and 300 mg), or a pharmaceutically acceptable salt thereof.

In another embodiment, a pharmaceutical composition of bupropion and DCS is administered to subjects on an acute basis, while bupropion, or a pharmaceutically acceptable salt thereof, is administered on days when the combination of DCS and bupropion is not administered to the subject. A pharmaceutical kit is contemplated comprising a multitude of pills of two types:

Dosage Type 1, comprising an effective amount of bupropion hydrochloride (between 30 mg and 300 mg), an effective amount of DCS (between 10 mg and 500 mg, preferably between about 25 mg and 250 mg), and inert ingredients; and Dosage Type 2, comprising an effective amount of bupropion hydrochloride (between 30 mg and 300 mg), and inert ingredients.

The different dosage units are arranged in a package, numbered serially, such that any two Dosage Type 1 units are separated by at least 3 Dosage Type 2 units, generally 5 to 10 Dosage Type 2 units. For example, a representative package would have Dosage Type 1 units slotted for administration on days 1, 8, 15, and 22, with Dosage Type 2 units provided for all other days.

In other methods of the invention, subjects are administered two separate pharmaceutical entities, one of which is a drug useful for treatment of female sexual dysfunction, and the second of which is a learning enhancer.

Insomnia

Pharmacologic agents useful for treatment of insomnia can be used in the methods of this invention. Zaleplon, zopiclone, and zolpidem are all central nervous system depressants indicated for treatment of insomnia. Benzodiazepines, e.g., lorazepam, clonazepam, oxazepam, flurazepam, triazolam, temazepam, alprazolam, and pharmaceutically acceptable salts thereof, are also frequently used to treat insomnia. Eszopiclone and indiplon are two other non-benzodiazepine compounds that are undergoing or have recently concluded clinical trials for treatment of insomnia.

Pharmaceutical combinations of (i) one or more cognitive enhancers, and (ii) one or more CNS depressants useful for treatment of insomnia, are contemplated according to the methods and compositions of the present invention. Administering said combinations to subjects can benefit subjects by consolidating the effects of the insomnia drug, making recurrent insomnia less likely. In some embodiments, subjects can be administered DCS (10 mg to 500 mg, preferably between about 25 mg and 250 mg) in combination with one or more pharmacologic agents generally known to be useful for treatment of insomnia, including but not limited to zaleplon (between 5 mg and 40 mg), zopiclone (between 2.5 mg and 50 mg), zolpidem (between 2.5 mg and 40 mg), eszopiclone (between 1 mg and 10 mg), indiplon (between about 2.5 mg and 50 mg), triazolam (between about 0.05 mg and 1 mg), clonazepam (between about 0.1 mg and 2 mg), alprazolam (between about 0.1 mg and 2.5 mg), lorazepam (between about 0.5 mg and 2.5 mg) and pharmaceutically acceptable salts thereof.

Multiple types of combinations are contemplated by the methods and compositions of this invention. For example, eszopiclone is routinely administered at a dose of 2 mg or 3 mg. In one embodiment, a pharmaceutical kit is contemplated comprising a multitude of pills of two types:

Dosage Type 1, comprising a therapeutically effective amount of eszopiclone (between 1 mg and 10 mg, preferably between 2 mg and 3 mg), DCS (between 10 mg and 500 mg, preferably between about 25 mg and 250 mg), and inert ingredients; and Dosage Type 2, comprising a therapeutically effective amount of eszopiclone (between 1 mg and 10 mg, preferably between 2 mg and 3 mg), and inert ingredients. The different dosage units would be arranged in a package, numbered serially, such that any two Dosage Type 1 units would be separated by at least 3 Dosage Type 2 units, generally 6 to 10 Dosage Type 2 units. For example, a representative package would have Dosage Type 1 units slotted for administration on days 2, 8, 16, and 25, with Dosage Type 2 units provided for all other days.

The methods of the invention can also be practiced by providing two distinct drug entities. For example, a subject with chronic insomnia can be prescribed two different drug entities. One is a standard treatment for insomnia, e.g., indiplon, 20 mg per day, or zolpidem tartrate, 10 mg per day; the second drug entity is DCS formulated in a pharmaceutical kit comprising dosages of two types:

Dosage Type 1, comprising an effective amount of DCS (between 10 mg and 500 mg, preferably between about 25 mg and 250 mg), and inert ingredients; and Dosage Type 2, comprising only inert ingredients. The different dosage units would be arranged in a package, numbered serially, such that any two Dosage Type 1 units would be separated by at least 3 Dosage Type 2 units, generally 5 to 10 Dosage Type 2 units. For example, a representative package would have Dosage Type 1 units slotted for administration on days 5, 12, 19, and 26, with Dosage Type 2 units provided for all other days. The subject would take both drugs on a daily basis, meaning the subject would ingest a conventional insomnia therapeutic on a daily basis, as well as a second pill containing either DCS or a placebo.

In another embodiment of the invention, the subject takes a pharmacologic agent useful for treatment of insomnia (e.g., zolpidem tartrate, between 2.5 and 20 mg, preferably between 5 mg and 10 mg) on a daily basis, and the subject additionally is administered DCS (between 10 mg and 500 mg, preferably between about 25 mg and 250 mg) one day per week.

In other embodiments of the invention, the subject takes a combination of DCS (10-500 mg, preferably 25-250 mg, even more preferably 25-100 mg) and a tricyclic antidepressant such as amitriptyline hydrochloride (between 5 mg and 500 mg, preferably between about 10 mg and 100 mg).

Pain

Many individuals suffer from chronic pain, often chronic neuropathic pain. While numerous non-pharmacologic techniques are used to treat neuropathic pain, including transcutaneous electrical nerve stimulation (TENS), acupuncture, physical therapy, and psychotherapy, pharmacotherapy may be the most widely used method for treating neuropathic pain, albeit with variable success. Medications from several different drug classes are commonly used to treat neuropathic pain, including topical agents, tricyclic antidepressants, serotonin specific reuptake inhibitors (SSRIs), anticonvulsants, and nonopioid analgesics.

Recent studies (*Science*, Vol 303, 1162-1167 (2004)) have demonstrated that people experience pain differently when they believe that the pain will be alleviated. The experience of pain arises from both physiological and psychological factors, including one's beliefs and expectations. Thus, placebo treatments that have no intrinsic pharmacological effects may produce analgesia by altering expectations. In two functional magnetic resonance imaging (fMRI) experiments, researchers found that placebo analgesia was related to decreased brain activity in pain-sensitive brain regions, including the thalamus, insula, and anterior cingulate cortex, and was associated with increased activity during anticipation of pain in the prefrontal cortex, providing evidence that placebos alter the experience of pain.

Given this result, it is clear that a subject's response to painful stimuli is governed by a number of factors, many of which are psychological. If a subject is anxious about the pain, the pain that is experienced in normally worse than if the subject is not anxious about the pain. It is not surprising, therefore, that chronic pain has been treated effectively using cognitive behavioral therapy. Administration of a drug that reduces pain will alter a subject's response to pain in a beneficial manner. By co-administering DCS, we will consolidate that beneficial response, reducing the likelihood of future deleterious responses to potential pain.

Neuropathic pain or chronic pain has been treated with various drugs including gabapentin, pregabalin, desipramine, amitryptiline, nortriptyline, fluoxetine, paroxetine, sertraline, fluvoxamine, citalopram, venlafaxine, tramadol, and phenyloin. In some embodiments of the invention, the anxiety component associated with neuropathic pain can potentially be eliminated by treating subjects with a combination of DCS (between 10 mg and 500 mg, preferably between about 25 mg and 250 mg) and one or more drugs selected from the group consisting of gabapentin (100 mg to 4000 mg total dosage per day), pregabalin (50 mg to 1000 mg total dosage per day), desipramine (10 mg to 300 mg total dosage per day), amitryptiline (5 mg to 500 mg total dosage per day), nortriptyline (5 mg to 400 mg total dosage per day), paroxetine (total dosage between 5 mg and 100 mg per day, preferably between 10 mg and 40 mg per day), sertraline (total dosage between 10 mg and 200 mg per day), citalopram (total dosage between 10 and 100 mg per day, preferably between 20 mg and 60 mg per day), fluoxetine (total dosage between 10 mg and 80 mg per day), fluvoxamine (total dosage between 25 mg and 300 mg per day), venlafaxine (total dosage between 5 mg and 300 mg per day), and tramadol (total dosage between 10 mg and 200 mg per day). Other potential drugs that can be combined with DCS or other learning enhancers to produce a pharmaceutical combination useful for alleviating neuropathic pain according to the methods of the invention include any other pharmaceuticals useful for treatment of chronic pain (e.g., aspirin, acetaminophen, ibuprofen, as well as more powerful analgesics, including narcotics) provided they do not significantly diminish the enhanced cognition attributable to treatment with the compound that enhances learning.

Multiple combinations are contemplated by the methods and compositions of this invention for alleviating chronic pain or neuropathic pain. Gabapentin is routinely administered at a variety of doses, depending on subject response. In one embodiment, a pharmaceutical kit is contemplated comprising a multitude of pills of two types:

Dosage Type 1, comprising an effective amount of gabapentin (100-1200 mg) an effective amount of DCS (between 10 mg and 500 mg, preferably between about 25 mg and 250 mg), and inert ingredients; and Dosage Type 2, comprising an effective amount of gabapentin and inert ingredients.

Gabapentin is typically dosed three times daily, so in this case, the different dosage units would be arranged in a package, numbered serially, such that any two Dosage Type 1 units would be separated by at least 9 Dosage Type 2 units, generally 21 to 30 Dosage Type 2 units. For example, a representative package would have Dosage Type 1 units slotted for administration at day 2, day 8, day 16, and day 25 (corresponding, for example, to pills 6, 23, 47, and 75), with Dosage Type 2 units provided for all other days. It is also contemplated that DCS could also be included in two successive pills, delivered eight hours apart.

The methods of the invention can also be practiced by providing two distinct formulated pharmaceuticals. For example, a subject suffering from neuropathic pain or other chronic pain can be prescribed two different formulated pharmaceuticals. One such pharmaceutical would be a standard treatment for the pain, such as gabapentin, pregabalin, or amitriptyline. The second pharmaceutical would be DCS in a pharmaceutical kit comprising dosages of two types:

Dosage Type 1, comprising an effective amount of DCS (between 10 mg and 500 mg, preferably between about 25 mg and 250 mg), and inert ingredients; and Dosage Type 2, comprising only inert ingredients.

The different dosage units would be arranged in a package, numbered serially, such that any two Dosage Type 1 units would be separated by at least 3 Dosage Type 2 units, generally 5 to 10 Dosage Type 2 units.

On a daily basis, the subject would ingest both types of pharmaceuticals, thereby receiving a pill for pain (e.g., gabapentin, amitriptyline, pregabalin) and a pill from the pharmaceutical kit (containing either DCS or placebo).

Extended-release versions of gabapentin are also contemplated, and can be useful in combination with DCS according to the methods of the invention.

In another embodiment, a pharmaceutical kit comprises a multitude of pills of two types:

Dosage Type 1, comprising an effective amount of amitriptyline (e.g., 20 mg) an effective amount of DCS (e.g., 50 mg), and inert ingredients; and Dosage Type 2, comprising an effective amount of amitriptyline (e.g., 20 mg) and inert ingredients.

The different dosage units are arranged in a package, numbered serially, such that any two Dosage Type 1 units are separated by at least 3 Dosage Type 2 units, generally 5 to 10 Dosage Type 1 units. For example, a representative package has Dosage Type 1 units slotted for administration on days 1, day 8, day 14, and 23; with Dosage Type 2 units provided for all other days.

In another embodiment of the invention, the subject would take a pharmacologic agent for treatment of chronic pain (e.g., amitriptyline, between about 5 mg and 100 mg) on a daily basis, and the subject would take a DCS tablet (between 10 mg and 500 mg, preferably between about 25 mg and 250 mg) one day per week.

Depression

The standard first-line pharmaceutical treatment for depression consists of administration of selective serotonin reuptake inhibitors (SSRIs) such as fluoxetine, paroxetine, sertraline and fluvoxamine. SSRIs are routinely administered on a daily basis for extended periods of time. While approved SSRIs provide added benefits relative to placebo alone, many clinical studies have shown that, with respect to health benefits for depression subjects enrolled in clinical studies, the difference between subjects taking FDA-approved SSRIs and those taking a placebo is less than the difference between subjects taking placebo and control subjects not receiving any treatment. In other words, for many subjects taking SSRIs, the psychological benefits derived from the subject's expectation of success outweighed the physiological benefits resulting from the biochemical effects of the drug. Other pharmacologic agents routinely prescribed for depression and anxiety disorders include tricyclic antidepressants.

Multiple combinations are contemplated in the methods and compositions of this invention. For example, sertraline is routinely administered at doses of 50 mg, 100 mg or 200 mg. In one embodiment, a pharmaceutical kit is contemplated comprising a multitude of pills of two types:

Dosage Type 1, comprising an effective amount of sertraline (preferably between 10 mg and 200 mg), an effective amount of DCS (between 10 mg and 500 mg, preferably between about 25 mg and 250 mg), and inert ingredients; and Dosage Type 2, comprising an effective amount of sertraline (preferably between 10 mg and 200 mg) and inert ingredients.

The different dosage units are arranged in a package, numbered serially, such that any two Dosage Type 1 units are separated by at least 3 Dosage Type 2 units, generally 5 to 10 Dosage Type 2 units. For example, a representative package would have Dosage Type 1 units slotted for administration at day 2, day 8, day 16, and day 25, with Dosage Type 2 units provided for all other days.

The methods of the invention can also be practiced by providing two distinct pharmaceutical formulations. For example, a subject with depression or social phobia can be prescribed two different pharmaceutical formulations. The first such formulation is a standard SSRI treatment for the condition, e.g., paroxetine, total dosage between 5 mg and 100 mg per day, preferably between 10 mg and 40 mg per day; or sertraline, total dosage between 10 mg and 200 mg per day; or citalopram, total dosage between 10 and 100 mg per day, preferably between 20 mg and 60 mg per day; or fluoxetine, total dosage between 10 mg and 80 mg per day; or fluvoxamine, total dosage between 25 and 300 mg per day; the second drug is DCS in a pharmaceutical kit comprising dosages of two types:

Dosage Type 1, comprising an effective amount of DCS (25-500 mg, preferably 50-100 mg), and inert ingredients; and Dosage Type 2, comprising only inert ingredients.

The different dosage units would be arranged in a package, numbered serially, such that any two Dosage Type 1 units would be separated by at least 3 Dosage Type 2 units, generally 5 to 10 Dosage Type 2 units. For example, a representative package would have Dosage Type 1 units slotted for administration on days 5, 12, 19, and 26, with Dosage Type 2 units provided for all other days.

The subject would take both drugs on a daily basis, meaning the subject would ingest a conventional SSRI therapeutic on a daily basis, as well as a second pill comprising either DCS or a placebo.

In another embodiment of the invention, the subject would take an SSRI therapeutic (e.g., sertraline, 100 mg) on a daily basis, and the subject would take a DCS tablet one day per week.

In other embodiments of the invention, subjects are administered a combination of DCS and a tricyclic antidepressant. In preferred embodiments, the tricyclic antidepressant is selected from the group consisting of amitriptyline, imipramine, desipramine, nortriptyline, and doxepin.

Attention-Deficit Hyperactivity Disorder (ADHD)

In order to improve upon conventional therapies for ADHD, subjects may be administered one or more compounds that enhance learning in combination with one or more compounds known to be useful for alleviating ADHD, including methylphenidate, atomoxetine, and ADDERALL XR® (a mixture of amphetamine salts available from Shire U.S. Inc., Wayne, Pa.). In these pharmaceutical combinations, the compounds that enhance learning act to consolidate the preferred behavioral response arising from treatment with the ADHD drug.

The methods of the invention can also be practiced by providing two distinct drug entities. For example, a subject with ADHD can be prescribed two different drug entities. One is a standard SSRI treatment for the condition, e.g., methylphenidate (10-40 mg, two doses per day), atomoxetine (10-60 mg, one or two doses per day), or a mixture of amphetamine salts (5-30 mg per day); the second drug is DCS in a pharmaceutical kit comprising dosages of two types:

Dosage Type 1, comprising an effective amount of DCS (10-500 mg, preferably between 0.5 mg/kg body weight and 2.0 mg/kg body weight), and inert ingredients; and Dosage Type 2, comprising only inert ingredients.

The different dosage units are arranged in a package, numbered serially, such that any two Dosage Type 1 units are separated by at least 3 Dosage Type 2 units, generally 5 to 10 Dosage Type 2 units. For example, a representative package would have Dosage Type 1 units slotted for administration at day 5, day 12, day 19, and day 26, with Dosage Type 2 units provided for all other days.

The subject would take both drugs on a daily basis, meaning the subject would ingest a conventional pharmacologic agent for treatment of ADHD on a daily basis (meaning multiple times per day, or once daily for some of the sustained release products), as well as a second pharmacologic agent comprising either DCS or a placebo.

In another embodiment of the methods of the invention, the subject would take methylphenidate twice per day, and would take a DCS pill on a weekly basis.

Formulation of Pharmaceutical Compositions

Pharmaceutical compositions contemplated by the methods and compositions of the invention may be formulated and administered to a subject for treatment of the diseases or afflictions disclosed herein as described below.

The invention encompasses the preparation and use of pharmaceutical compositions comprising a compound (or combinations of compounds) useful for treatment of the diseases and disorders disclosed herein as an active ingredient. Such a pharmaceutical composition may consist of the active ingredient(s) alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

The compounds of the invention are also useful when formulated as salts. In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable acid addition salts of inorganic acids may also be formed, including hydrochloride, sulfate, nitrate, bicarbonate, and carbonate salts. Pharmaceutically acceptable salts may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

The descriptions of pharmaceutical compositions provided herein are directed to pharmaceutical compositions which are suitable for ethical administration to humans.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The active ingredient combinations of the invention can be provided as components of a pharmaceutical pack. The two drugs can be formulated together or separately and in individual dosage amounts.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

The therapeutically effective dose of the pharmacologic agent can be administered using any medically acceptable mode of administration. Although the skilled artisan would contemplate any of the modes of administration known to one of ordinary skill, preferably the pharmacologic agent is administered according to the recommended mode of administration, for example, the mode of administration listed on the package insert of a commercially available agent.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken, i.e., by rapid inhalation through the nasal passage from a container of the powder.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

The active ingredient combinations of the invention can be provided as components of a pharmaceutical pack, referred to herein as a "kit". The two drugs can be formulated together or separately and in individual dosage amounts.

Specifically, the present invention contemplates a kit comprising two different dosage types arranged in the package for successive daily oral administration: Dosage Type 1, which includes a compound that enhances learning, and Dosage Type 2, which lacks a compound that enhances learning. The dosages are taken on a daily basis, with Dosage Type 1 units separated from other Dosage Type 1 units by at least three Dosage Type 2 units, typically between 5 and 10 Dosage Type 2 units.

In the simplest embodiment, DCS is the only active ingredient in the Dosage Type 1 units, and the Dosage Type 2 units have no active ingredient. This embodiment is useful because the formulation could be combined effectively with daily administration of many different pharmaceutical remedies: Other representative embodiments are shown in the table below:

| Dosage Type 1 Active Ingredients | Dosage Type 2 Active Ingredients |
|---|---|
| Gabapentin, DCS | Gabapentin |
| Pregabalin, DCS | Pregabalin |
| Methylphenidate, DCS | Methylphenidate |
| Zaleplon, DCS | Zaleplon |
| Zolpidem, DCS | Zolpidem |
| Pregabalin, D-Serine | Pregabalin |
| Methylphenidate, D-Serine | Methylphenidate |
| Zaleplon, D-Serine | Zaleplon |
| Zolpidem, ACPC | Zolpidem |
| Zopiclone, DCS | Zopiclone |
| Indiplon, DCS | Indiplon |
| Eszopiclone, DCS | Eszopiclone |
| Fluoxetine, DCS | Fluoxetine |
| Fluvoxamine, DCS | Fluvoxamine |
| Paroxetine, DCS | Paroxetine |
| Sertraline, DCS | Sertraline, |
| Citalopram, DCS | Citalopram |
| Escitalopram, DCS | Escitalopram |
| Amphetamine, Dextroamphetamine, DCS | Amphetamine, Dextroamphetamine |
| Nortriptyline, DCS | Nortriptyline |
| Amitriptyline, DCS | Amitriptyline |

-continued

| Dosage Type 1 Active Ingredients | Dosage Type 2 Active Ingredients |
|---|---|
| Desipramine, DCS | Desipramine |
| Bupropion, DCS | Bupropion |
| Atomoxetine, DCS | Atomoxetine |
| Clonazepam, DCS | Clonazepam |
| Alprazolam, DCS | Alprazolam |

Dosage

For compounds that enhance learning, dosage levels can be between about 0.1 mg and 5 g when administered to adult subjects. In one embodiment, when the learning enhancer is D-serine, the contemplated dose is between about 50 mg and 5 g when administered to adult subjects.

When the learning enhancer is DCS, dosage levels can be between about 5 mg and 1 g, generally between 25 mg and 500 mg when administered to adult subjects. The therapeutically effective dose of the pharmacologic agent can be administered using any medically acceptable mode of administration. Although the skilled artisan would contemplate any of the modes of administration known to one of ordinary skill, preferably the pharmacologic agent is administered according to the recommended mode of administration, for example, the mode of administration listed on the package insert of a commercially available agent. Dosage levels of DCS between about 5 mg and 150 mg may be advantageous because such dosages provide sufficient learning enhancement to consolidate the desired response, but are less likely to have side effects. Dosage levels of DCS between about 25 mg and 100 mg may be advantageous because such dosages provide sufficient learning enhancement to consolidate the desired response, but are less likely to have side effects. Dosage levels of DCS between 25 mg and 100 mg will be sub-antimicrobial (i.e., dosage does not kill or significantly restrict growth of bacteria) in strength toward most bacteria; in particular, dosages between 25 mg and 75 mg will be sub-antimicrobial in strength against a greater percentage of bacteria, and dosages between 25 mg and 50 mg will be sub-antimicrobial in strength against an ever greater percentage of bacteria.

Dosage levels of the primary drug useful for alleviating the recurrent medical affliction include any therapeutically effective dosages of the primary drugs approved by the FDA. Generally, these doses will be between about 0.1 mg and 5 g.

EXAMPLES

The invention is now described with reference to the following examples. These examples are provided for the purpose of illustration only and the invention should in no way be construed as being limited to these examples but rather should be construed to encompass any and all variations which become evident as a result of the teaching provided herein.

Pharmaceutical compositions of the invention are further illustrated by the following examples without limiting the scope of invention. Examples 5 through 16 are prophetic examples.

All FDA-approved pharmacologic agents used in the following examples were obtained from commercial suppliers and/or pharmacies. All active ingredients used in human subjects in the following examples have been approved for use in humans by the FDA. Capsules containing mixtures of multiple active ingredients were obtained by measuring out solid powders or granulates of the active ingredients and loading them into the capsules.

Example 1

A subject afflicted with recurring neuropathic pain was treated for seven days with 10 mg per day amitriptyline hydrochloride, with little effect on the pain. After seven days, the dose of amitriptyline was doubled to 20 mg. After two days on the higher dose, the subject's pain substantially subsided. The subject was subsequently treated with a single dose of a capsule containing 20 mg amitriptyline, 25 mg DCS, and pharmaceutically inactive ingredients. Subsequently, the subject reverted to taking 20 mg amitriptyline (with no DCS) until the amitriptyline treatment had been ongoing for a period of four weeks, before tapering the dose down and then stopping treatment.

Example 2

A powdered blend of 10 mg zolpidem tartrate and 50 mg DCS, in addition to the following inactive ingredients: hydroxypropyl methylcellulose, lactose, magnesium stearate, microcrystalline cellulose, polyethylene glycol, sodium starch glycolate, and titanium dioxide, was mixed and loaded into a capsule. The capsule was administered to a subject afflicted with recurring transient insomnia. After taking the capsule, the subject experienced a short sleep onset, as well as good sleep quality. For the next five nights, the subject was administered a capsule containing 5 mg zolpidem tartrate, without co-administration of DCS. On the seventh night, the subject was administered a single capsule containing 5 mg zolpidem tartrate and 50 mg DCS, in addition to the following inactive ingredients: hydroxypropyl methylcellulose, lactose, magnesium stearate, microcrystalline cellulose, polyethylene glycol, sodium starch glycolate, and titanium dioxide. The subject discontinued further treatment. The subject's anxiety regarding sleep, particularly after awakening in the middle of the night, was reduced, and the subject found it easier to revert to a sleeping state.

Example 3

A powdered blend of sildenafil citrate (50 mg) and DCS (50 mg), as well as inactive ingredients including: microcrystalline cellulose, dibasic calcium phosphate, croscarmellose sodium, magnesium stearate, hydroxypropyl methylcellulose, titanium dioxide, lactose, and triacetin, was mixed and loaded into a capsule.

Example 4

A healthy volunteer subject was administered a capsule containing about 50 mg sildenafil citrate and 50 mg DCS, in addition to inactive ingredients. The pharmaceutical composition was assessed for adverse effects or reactions in the subject, of which none were reported. The pharmaceutical composition was also assessed for its effects on sexual performance enhancement.

Example 5

The following components are sieved and mixed intimately: DCS (200 g), sildenafil citrate (50 g), a mixture of lactose and microcrystalline cellulose (700 g), polyvinyl pyrrolidone (100 g), cellulose ether (100 g), silicon dioxide (4 g). Magnesium stearate is also sieved and admixed to the mixture of the other components. The composition is tableted directly to produce tablets weighing 1.16 g. After pressing, the tablet core is coated with an aqueous film. The film thickness is variable.

Example 6

A mixture of 50 g of DCS, 20 g tadalafil, 75 g of lactose and 100 g of talc is combined, mixed, wetted with a sufficient quantity of alcohol and granulated followed by drying. The obtained granulate can be either pressed to form tablets or filled into capsules containing 50 mg DCS and 20 mg vardenafil. The pharmaceutical compositions can be useful for alleviating erectile dysfunction.

Example 7

A mixture of 125 g of DCS, 20 g vardenafil HCl, 75 g of lactose and 100 g of talc is combined, mixed, wetted with a sufficient quantity of alcohol and granulated followed by drying. The obtained granulate is either pressed to form tablets or filled into capsules containing 125 mg DCS and 20 mg vardenafil. The pharmaceutical compositions can be useful for alleviating erectile dysfunction.

Example 8

A mixture of 50 g of DCS, 5 g of zolpidem tartrate, 50 g of lactose and 75 g of talc is combined, mixed, wetted with a sufficient quantity of alcohol and granulated followed by drying. The obtained granulate is either pressed to form tablets or filled into capsules containing 50 mg DCS and 5 mg zolpidem tartrate. The pharmaceutical compositions can be useful for alleviating insomnia.

Example 9

Tablets containing amitriptyline and DCS (75 mg) are formed from standard pharmaceutical excipients using standard technology for forming tablets. The tablets can be useful for alleviating one or more of the following recurrent medical afflictions: neuropathic pain, insomnia, and depression.

Example 10

Erectile dysfunction has been shown to be responsive to pharmacological treatment with PDE-5 inhibitors such as sildenafil. In the randomized, placebo-controlled clinical study described below, acute treatment with an NMDA partial receptor agonist is used to enhance the effects of treatment of erectile dysfunction with a PDE-5 inhibitor.

There are three arms to the study: subjects taking placebo only, subjects taking a PDE-5 inhibitor only, and subjects taking a combination of a PDE-5 inhibitor and DCS. Specifically, combination therapy subjects are administered a capsule containing a combination of sildenafil citrate (50 mg) and DCS (75 mg). Mono-drug therapy subjects are administered a capsule containing sildenafil citrate (50 mg). Subjects are classed into three different categories (organic, psychogenic, mixed) based on etiologies of erectile dysfunction. All subjects are told that they will be in a clinical trial, with various arms, studying the ability of a new drug to alleviate erectile dysfunction. The study has a projected duration of nine months.

Analogous to previous clinical studies for erectile dysfunction, the effects of treatments are assessed for the men's abilities to engage in sexual activity and to achieve and maintain erections sufficient for satisfactory sexual activity. Subject self-assessment of sexual function, at baseline and during and after the study, is used to evaluate the success of the therapy. Two important end-point questions are frequency of successful penetration during sexual activity and maintenance of erections after penetration. After six months on the drug therapy, the drug therapy is ended, and the subjects are evaluated, using the same sexual function criteria, for the next three months, a period during which the subjects do not take drugs for erectile dysfunction.

Subsequent studies may target erectile dysfunction subjects by classifications such as disease etiology, age, or whether or not the subject has had prostate cancer.

Example 11

Insomnia has been shown to be responsive to pharmacological treatment with compounds such as zolpidem tartrate. In the randomized, placebo-controlled clinical study described below, acute treatment with an NMDA glutamate receptor agonist is used to enhance the effects of treatment of chronic insomnia with zolpidem tartrate.

There are three arms to the study: subjects taking placebo only, subjects taking only zolpidem tartrate (10 mg daily), and subjects taking a combination of zolpidem tartrate and DCS. Specifically, combination therapy subjects are treated via daily administration of one of two types of pharmaceuticals. On days 2-7, 9-14, 16-21, and 23-28, the subjects ingest a capsule containing zolpidem tartrate (10 mg) as the only active ingredient. On days 1, 8, 15, and 29, subjects ingest a capsule containing both zolpidem tartrate (10 mg) and DCS (50 mg). All subjects are told that they will be in a clinical trial, with various arms, studying the ability of a new drug to alleviate insomnia. Sleep latency and sleep efficiency are evaluated in the subjects.

Subject self-assessment of insomnia is also used to evaluate the success of the therapy. A follow-up evaluation of subjects is conducted after three months. Endpoint questions include frequency of insomnia and duration of insomnia.

Example 12

Clinical depression has been shown to be responsive to pharmaceutical treatment with SSRIs. Many subjects whose symptoms are alleviated by SSRIs would like to go off their medications without experiencing a revival of their symptoms. In the treatment protocol described below, a subject who responds positively to treatment with fluoxetine is also treated with DCS on an intermittent basis.

A subject suffering from depression is treated on a daily basis for 30 days by being administered two pharmacologic agents:

1. a coated tablet containing either DCS (100 mg) or placebo; and
2. fluoxetine, 20 mg.

The first pharmacologic agent comes in a serially numbered pharmaceutical kit, with DCS tablets corresponding to days 5, 15, and 25, and placebo tablets on all other days. The placebo tablets and DCS tablets are visually indistinguishable.

Relative to subjects treated with fluoxetine alone, a subject receiving the combination therapy should, on average, have reduced anxiety, and is less likely to experience a recurrence of the condition sufficient to require additional drug therapy.

Example 13

A subject suffering from chronic insomnia is treated on a daily basis for 30 days by being administered two pharmacologic agents:

(1) a coated tablet containing either DCS (100 mg) or placebo; and (2) indiplon, 20 mg The first pharmacologic agent (i.e., the coated table containing DCS or placebo) is provided comes in a pharmaceutical kit comprising a serially numbered package, with DCS tablets corresponding to days 3, 10, 17, and 24; and placebo tablets on all other days. The placebo tablets and DCS tablets are visually indistinguishable.

Relative to subjects treated with indiplon alone, a subject receiving the combination therapy will be less likely to experience a recurrence of the condition sufficient to require additional drug therapy.

Example 14

A subject suffering from neuropathic pain and sleeping difficulties is administered amitriptyline (20 mg) on a daily basis for 30 days. Every seven days, the subject is additionally treated with DCS (50 mg). Relative to subjects treated with amitriptyline alone, the subject treated additionally with DCS on an acute basis will be more likely to experience a more positive pharmacotherapy outcome, resulting in an increased alleviation of neuropathic pain and/or sleeping problems.

Example 15

A subject suffering from neuropathic pain is treated daily for 30 days with pharmaceutical tablets arranged in a serially numbered package comprising tablets of the following two types:

(1) amitriptyline (20 mg) and DCS (50 mg)

(2) amitriptyline (20 mg)

The two types of tablets are indistinguishable. The combination tablets containing both amitriptyline and DCS correspond to days 3, 10, 17, and 24 in the numbered package, with amitriptyline tablets (not containing DCS) provided for all other days in the pharmaceutical kit.

Relative to subjects treated with amitriptyline alone, a subject receiving the combination therapy will be more likely to experience a greater decrease in neuropathic pain, on either a temporary or long-term basis.

Example 16

An array of 28 coated tablets is incorporated in a numbered blister pack. The 28 tablets include 4 tablets containing DCS (100 mg) and conventional pharmaceutical excipients, and 24 placebo tablets containing conventional pharmaceutical excipients but lacking DCS. All coated tablets are visually indistinguishable. The DCS tablets are positioned in numerical slots 1, 9, 18, and 27. The blister pack includes directions informing a subject that if he or she has forgotten to take a tablet on one day, the proper course of action is to take two tablets the following day.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. Although the foregoing invention has been described in some detail by way of illustration and example for purposes of clarity of understanding, it will be obvious that certain changes and modifications may be practiced within the scope of the representative embodiments of these concepts presented below. The appended claims are intended to be construed to include all such embodiments and equivalent variations.

We claim:

1. A method for treating erectile dysfunction in a subject which comprises administering to the subject a therapeutically effective amount of:
   (i) D-cycloserine, or a pharmaceutically acceptable salt thereof; and
   (ii) a pharmacologic agent or pharmaceutically acceptable salt thereof selected from the group consisting of sildenafil, tadalafil, and vardenafil;
   wherein said pharmacologic agent or pharmaceutically acceptable salt thereof selected from the group consisting of sildenafil, tadalafil, and vardenafil is administered to the subject prior to sexual activity, and wherein said D-cycloserine is administered to the subject within 12 hours of the administration of said pharmacologic agent or pharmaceutically acceptable salt thereof selected from the group consisting of sildenafil, tadalafil, and vardenafil.

2. The method of claim 1, wherein said D-cycloserine or pharmaceutically acceptable salt thereof is administered at a dose of between about 0.25 mg/kg and 10 mg/kg body weight of the subject.

3. The method of claim 1, wherein said D-cycloserine or pharmaceutically acceptable salt thereof is administered to the subject on an acute basis.

* * * * *